(12) United States Patent
Hackel et al.

(10) Patent No.: US 9,603,530 B2
(45) Date of Patent: *Mar. 28, 2017

(54) DENTAL SYSTEM FOR TRANS-ILLUMINATION OF TEETH

(71) Applicant: KALTENBACH & VOIGT GMBH, Biberach (DE)

(72) Inventors: André Hackel, Biberach (DE); Hans Heckenberger, Assmannshardt (DE); Sven Erdmann, Ulm (DE)

(73) Assignee: KALTENBACH & VOIGT GMBH, Biberach (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/197,237

(22) Filed: Jun. 29, 2016

(65) Prior Publication Data

US 2016/0310009 A1    Oct. 27, 2016

Related U.S. Application Data

(63) Continuation of application No. 13/291,798, filed on Nov. 8, 2011, now Pat. No. 9,380,943.

(30) Foreign Application Priority Data

Nov. 11, 2010   (DE) .................. 10 2010 043 792

(51) Int. Cl.
*A61B 5/00* (2006.01)
*A61B 1/00* (2006.01)
(Continued)

(52) U.S. Cl.
CPC ........ *A61B 5/0088* (2013.01); *A61B 1/00096* (2013.01); *A61B 1/00101* (2013.01); *A61B 1/00186* (2013.01); *A61B 1/0676* (2013.01); *A61B 1/07* (2013.01); *A61B 1/24* (2013.01); *A61B 2562/0238* (2013.01)

(58) Field of Classification Search
CPC ........... A61B 1/00096; A61B 1/00101; A61B 1/00186; A61B 1/0676; A61B 1/07; A61B 1/24; A61B 2562/0238; A61B 5/0088
See application file for complete search history.

(56) References Cited

U.S. PATENT DOCUMENTS 4,184,175 A    1/1980  Mullane, Jr.
5,290,168 A *  3/1994  Cooper .............. A61B 1/00091
                                                348/E5.029

(Continued)

FOREIGN PATENT DOCUMENTS

DE    10 2006 041 020 A1    3/2008

*Primary Examiner* — Ruth S Smith
(74) *Attorney, Agent, or Firm* — Marshall, Gerstein & Borun LLP

(57) ABSTRACT

A dental system may trans-illuminate teeth using a light source for producing examination radiation by directing the examination radiation at a tooth to be examined. An optical image of the tooth illuminated by the examination radiation may be acquired. The light source may include a light-guiding and/or light-deflecting element that faces the tooth to be examined being embedded in a transparent. The light-guiding and/or light-deflecting element may be embedded in a transparent, flexible coupling body that is provided to rest on the tooth or the gingiva of the tooth.

17 Claims, 6 Drawing Sheets

(51) Int. Cl.
*A61B 1/06* (2006.01)
*A61B 1/24* (2006.01)
*A61B 1/07* (2006.01)

(56) References Cited

U.S. PATENT DOCUMENTS

| | | | | |
|---|---|---|---|---|
| 6,672,868 | B1* | 1/2004 | Momot | A61B 5/0088 |
| | | | | 382/100 |
| 6,957,907 | B2* | 10/2005 | Fischer | A61B 5/0088 |
| | | | | 362/16 |
| 2007/0241673 | A1 | 10/2007 | Yamada et al. | |
| 2008/0038686 | A1* | 2/2008 | Nagai | A61B 5/0088 |
| | | | | 433/29 |
| 2008/0248447 | A1* | 10/2008 | Karazivan | A61B 5/0088 |
| | | | | 433/215 |
| 2011/0300505 | A1* | 12/2011 | Jessop | A61C 19/004 |
| | | | | 433/29 |

* cited by examiner

DENTAL SYSTEM FOR TRANS-ILLUMINATION OF TEETH

BACKGROUND OF THE INVENTION

Field of the Invention

The present invention relates to a dental system for the transillumination of teeth. The system has a light source for producing examination radiation, irradiation means for directing the examination radiation at a tooth to be examined, and means for acquiring an optical image of the tooth illuminated by the examination radiation.

Related Technology

In medicine, in particular in dentistry, diagnostic systems based on optical principles are increasingly being used. The reason for this is that such devices usually allow a diagnosis to be made without contact, that is to say in particular in a pain-free manner, and, in addition, often also provide optical images with which any necessary therapeutic measures can be communicated to the patient graphically and hence more clearly. For example, so-called intraoral cameras are used in dentistry, which cameras include a handpiece, the front end region of which is introduced into the mouth of a patient. In that end region there is generally a light-entry or viewing window for the camera lens, from which the image of the object to be examined is transmitted to an acquisition device, for example a CCD chip.

Such an intraoral camera can further be extended to a system for the transillumination of teeth, as is known inter alia from DE 10 2006 041 020 A1 of the applicant. In that system, the tooth to be examined is irradiated with light within a specific wavelength range, an optical image of the tooth illuminated by the examination radiation then being acquired and evaluated. Because carious areas in the tooth scatter the light differently than healthy dental tissue, such areas can be identified when the tooth is observed with the aid of a camera, it even being possible, if the system is suitably configured, to obtain a more reliable caries diagnosis than is the case with a conventional X-ray examination.

The quality of the images produced in this procedure, and hence ultimately of the caries diagnosis, is dependent to a critical extent on the way in which the light is coupled into the tooth to be illuminated. In DE 10 2006 041 020 A1 there is used for that purpose a special head-piece of an instrument, which rests on the tooth. If excessive irradiation occurs as a result of illumination of the light sensor directly or by reflection, a computational elimination of those image regions is carried out. However, this has the disadvantage that the dynamic range of the system is limited on account of the computational possibilities.

As an alternative thereto there is known from U.S. Pat. No. 4,184,175 a polarizing filter for removing reflected light or direct light. However, the polarization causes a loss in intensity in the illumination of the tooth, which represents a not inconsiderable disadvantage. Finally, U.S. Pat. No. 6,672,868 describes a device which has mechanical means for blocking light, by which the direct ingress of reflected light or direct light in the light sensor is reduced. However, such measures result in an enlarged construction of the front end region of the device, which is a disadvantage because of the already restricted room for maneuver inside the oral cavity of the patient.

SUMMARY OF THE INVENTION

Accordingly, the object underlying the present invention is to provide a novel solution for the production of a system for the transillumination of teeth, in which the above-mentioned disadvantages are avoided. In particular, effective and reliable coupling of the light into the tooth that is to be transilluminated is to be ensured.

Accordingly, the invention provides a dental system for the transillumination of teeth, comprising:

a light source for producing examination radiation, irradiation means for directing the examination radiation at a tooth to be examined, and means for acquiring an optical image of the tooth illuminated by the examination radiation, wherein the irradiation means include light-guiding and/or light-deflecting elements, and at least the light-guiding and/or light-deflecting element facing the tooth to be examined is embedded in a transparent, flexible coupling body which is provided to rest on the tooth or on the gingiva of the tooth.

The solution according to the invention is based on the idea of optimizing the manner in which light is coupled into the tooth that is to be transilluminated. To that end, it is proposed according to a first aspect of the present invention to embed a light-guiding or light-deflecting element, which faces the tooth to be examined and with the aid of which the light is ultimately directed at the tooth, in a transparent, flexible coupling body which is provided to rest on the tooth or the gum, the so-called gingiva.

According to this first aspect of the present invention there is accordingly proposed a dental system for the transillumination of teeth which has a light source for producing examination radiation, irradiation means for directing the examination radiation at a tooth to be examined, and means for acquiring an optical image of the tooth illuminated by the examination radiation, wherein the irradiation means include light-deflecting and/or light-guiding elements and wherein at least the light-guiding and/or light-deflecting element facing the tooth to be examined is embedded in a transparent, flexible coupling body which is provided to rest on the tooth or on the gingiva of the tooth.

Because the coupling of light into the tooth is carried out with the aid of the flexible coupling body, the emergence of interfering light from the light-guiding element is prevented or at least reduced. A maximum degree of coupling of the light into the tooth substance or gingiva is obtained, which ultimately leads to improved images of the tooth to be examined.

The coupling geometry of the transparent coupling body can consist of a plane face, a sphere, a spherical segment, a concave or convex face or a free-form face. Those faces can then advantageously be equipped with an additional structure which prevents light that cannot be coupled into the hard tooth tissue and/or gingiva from being reflected at the tooth and/or gingiva and leading to overexposure of the image recording sensor or other light-sensitive detector. The mode of operation of this principle is based on the fact that light beams are partially deflected at the faces of the additional structure as long as the corresponding structures do not come into contact with the hard tooth tissue and/or gingiva. The effect is based on the difference in refractive index between the contact material and air, which allows light to exit the coupling body only at specific angles. If the structures of the coupling body are not resting on the tooth or gingiva, more light is reflected back, due to the conditions, and not decoupled. Geometries in the form of pyramids, cones, waves and waves with any desired suitable structure which is distributed periodically and/or non-periodically are suitable for these additional structures.

As well as improving the coupling of light into the tooth to be examined, a further function of the coupling body is to protect the light-guiding and/or light-deflecting elements, by means of which the light from the light source is directed at the tooth, from external influences. This is important because it is absolutely necessary for hygiene reasons regularly to clean, but in particular also to sterilize, the area of the device that is introduced into the oral cavity of the patient. By embedding the light-guiding/light-deflecting elements, they are better protected so that they are not damaged by the sterilizing operation, in which the device is exposed to high temperatures as well as to high humidity. It is possible in particular for light guides which extend from a light source to the light decoupling point to be embedded in the transparent material of the coupling body. At the frontmost end of the light guide there can be located a prism, which ultimately effects deflection of the beam in order to direct the light at the tooth to be examined. It has been shown that the protective action for the elements for light transmission can additionally be improved if a hydrophobic coating is used. This could be applied, for example, directly to the light guide or to a sheathing of the light guide, in order to prevent moisture from penetrating into the underlying components and damaging them. For example, the material Parylene could be used for this purpose.

A further advantageous measure of the present invention serves to avoid, or at least reduce, the formation of so-called speckle, which is caused by interference phenomena in human tissue. To that end, it is proposed to irradiate the tooth to be examined with a comparatively small spectral bandwidth in the range from 2 to 10 nm.

It is further possible according to the invention for a particular arrangement of the light sources inside the hand-held device to be provided. This particular arrangement is attributable to the fact that light guides are used for the transmission of the light but, owing to the space required for image transmission to the image acquisition means, they are not able to run centrally through the hand-held device. In that case, an inclined orientation of the light sources relative to the longitudinal axis of the handpiece has been found to be advantageous because, in that manner, maximum transmission of the emitted light can be achieved while, at the same time, the bending radius of the light guide can be optimized and—as will be explained in detail hereinbelow—as small a construction as possible for the handpiece is possible.

Finally, according to a further aspect of the present invention there is proposed a specially designed attachment for passing light through a tooth to be examined, in which the tooth is illuminated from one side and the image of the illuminated tooth is acquired from the opposite side. Because the attachment is mounted to be removable from the handpiece but is fixed relative to the longitudinal axis of the handpiece, the operation is made much easier and a substantial saving in terms of working time is achieved, because the viewing direction can be changed immediately.

Ultimately, because of the measures described above, on the one hand the quality of the images that can be obtained, and hence the reliability of the caries diagnosis, is improved and on the other hand handling of the device is simplified.

BRIEF DESCRIPTION OF THE DRAWINGS

The invention is to be explained in greater detail hereinbelow with reference to the accompanying drawing, in which.

DETAILED DESCRIPTION

The transillumination method on which the present invention is based will first be explained in principle.

The transillumination method is based on passing visible light through a tooth, that is to say transilluminating it. To that end, examination radiation is generated with the aid of a light source and is directed at the tooth. The examination radiation is usually in a wavelength range of approximately from 550 µam to 790 µm, for example approximately 670 µm. The tissue of the tooth does not completely block the examination radiation but instead allows the light to pass through the tooth. The radiation is thereby partially scattered, carious regions in particular having a characteristic effect on the light. If the tooth transilluminated in that manner is viewed from different viewing directions, such carious regions can be detected because they appear slightly darker. In particular when images taken at different times are compared with one another, caries can thus be detected comparatively effectively and also in good time.

Figure 1:
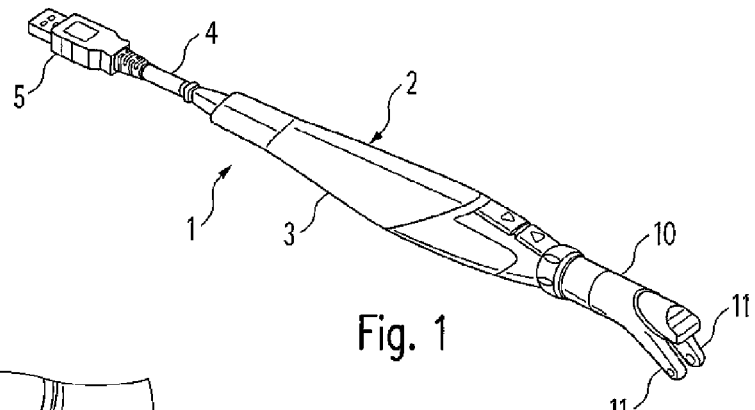
FIG. 1 shows a view of a first embodiment of a hand-held device for the transillumination of teeth.

A device using this principle is shown in FIG. 1 and is denoted generally by the reference numeral 1. It comprises as a fundamental component an elongate hand-held device 2 having a handle 3 in which the fundamental components for illuminating the tooth to be examined and for image acquisition are arranged. There are located inside the handle 3 in particular light sources for producing examination radiation, as well as image acquisition means, for example in the form of a CCD chip for recording an image of a tooth illuminated with the aid of the light. The data provided by the image acquisition means are then transmitted to a central processing unit. To that end, a cable 4, at the end of which there is a USB connector 5, extends from the rear end of the handle 3, via which cable 4 a connection to a PC can be made in a simple manner. The image information can then be stored and analyzed in the PC (not shown). Instead of the USB connector shown, the hand-held device 2 could also be connected to a central processing unit by other means. However, the USB connection has been found to be particularly advantageous because the device 1 can thereby at the same time also be supplied with power.

Figure 2:
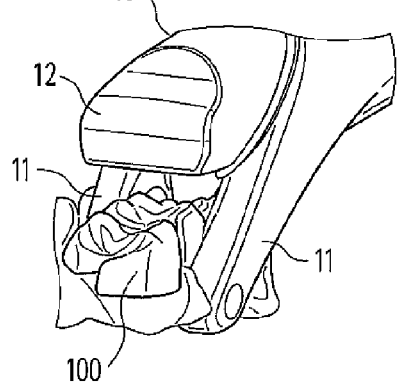
FIG. 2 shows an enlarged view of the front end region of the hand-held device.
Figure 2A:
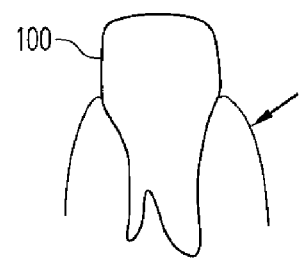
FIG. 2a shows schematically the coupling of the light into the gingiva.

The arrangement of the light sources and of the image acquisition means inside the handle 3 of the handpiece 2 firstly has the advantage that those components are here comparatively well protected from external influences. The actual illumination of the tooth is carried out with the aid of an attachment 10 which is detachably arranged at the front end of the handle 3. As is shown in the sectional view of FIG. 3, the handle 3 has at its front end a hollow-cylindrical pin 6 on which the attachment 10 is fitted. At the front end of the attachment 10 there are formed two lateral arms 11, via each of which, according to the representation of FIG. 2, the light can be directed at lateral surfaces of a tooth 100 to be examined or at the gum of the tooth 100, the so-called gingiva. As is shown in FIG. 2a, the light coupling is here ideally effected slightly obliquely in the upper end region of the gingiva, because it has been shown that the highest contrast for the transilluminated tooth 100 is achieved in that case. The more detailed configuration of the arms 11 with the elements for light transmission located therein will be explained in detail hereinbelow.

The light entry for observation of the illuminated tooth is carried out with the aid of a window formed on the underside of the front end region 12 of the attachment 10. The cylindrical pin 6 of the hand-held device 2 extends into the front end region 12 of the attachment 10 so that light is able to enter a deflecting prism 7 via the window. Incoming light beams are deflected by the deflecting prism 7 in such a manner that they are directed at the image acquisition means, that is to say, for example, the CCD chip 8, located in the handle 3. The deflecting prism 7 is so configured that a deflection of the beams by an angle of approximately 90°, preferably of slightly less than 90°, is achieved.

Figure 3:
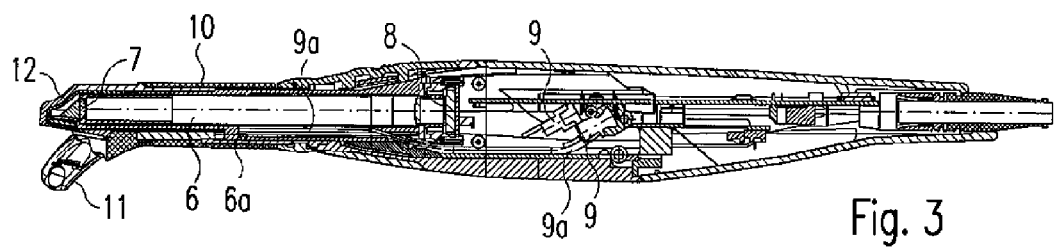
FIG. 3 shows a sectional view of the device of FIG. 1.

As is clear from FIG. 3, the image of the illuminated tooth 100 is accordingly reflected centrally through the hollow-cylindrical pin 6 to the CCD chip 8. This means that light guides for transmitting the light that extend along the handpiece 2 should, if possible, extend at the edge in order not to impair the transmission of the image. In order to achieve optimum light transmission, a special arrangement and orientation of the light sources and light guides is proposed, which is to be explained hereinbelow with reference to FIGS. 3 and 4.

The problem is that, for reasons of space, although the light sources, which are provided with the reference numeral 9 in the drawings, are to be arranged approximately centrally inside the handle 3, the light guides themselves are to extend at the edge. At the same time, however, the light guides are to be bent to only a specific radius in order to ensure optimum light transmission. To that end it is proposed to arrange the light sources 9 at an angle of approximately 50 to 60° relative to the longitudinal axis of the handpiece. This inclined position of the light sources 9 can be seen in particular in the view in FIG. 4, which shows the inclined placement of the light sources 9 on the plate for the camera electronics. This inclined position has the result that the bending radius of the light guide 9a extending immediately from the light sources to the front side of the handpiece 2 can be kept within a range in which maximum light transmission is ensured. At the same time, the dimensions of the handle 3 can be minimized so that a handpiece 2 that is comparatively compact and hence easy to handle is achieved. As an alternative to the embodiment shown, it is also possible for the light sources to be integrated into the housing of the handpiece 2. In that case, they are connected to the camera plate via an electric cable.

Figure 4:
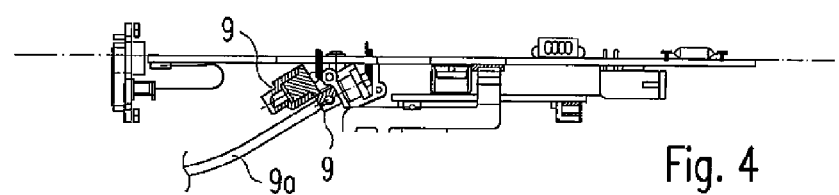
FIG. 4 shows a view of the arrangement of the light sources inside the hand-held device.
Figure 5:
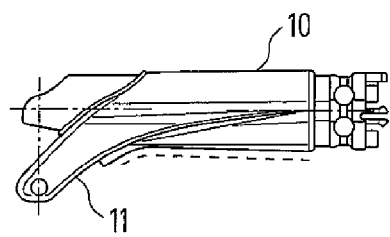
FIGS. 5-8 show different views of the front end region of the attachment of the hand-held device with the passage of the light guides used for light coupling.

The light guides 9a, one of which is shown in each of FIGS. 3 and 4, extend to a front shoulder 6a on the underside of the projection 6. When the attachment 10 is in the fitted state, the front ends of the light guides 9a are aligned with end faces of further light guides 9b, which extend inside the attachment 10 to its front end into the end regions of the two arms 11. This configuration and arrangement of these continuing light guides 9b is to be explained in greater detail hereinbelow with reference to FIGS. 5 to 15.

Figure 6:
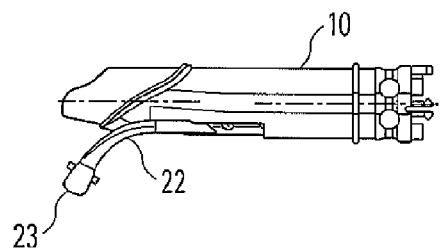
Figure 7:
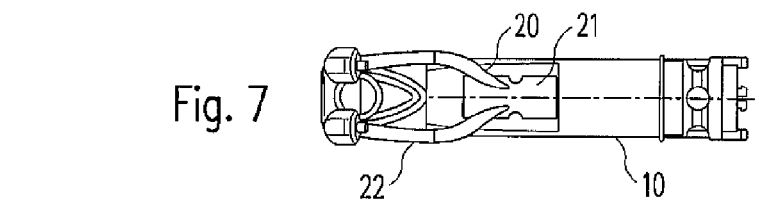
Figure 8:
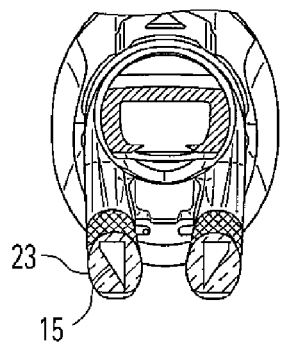
Figure 9:
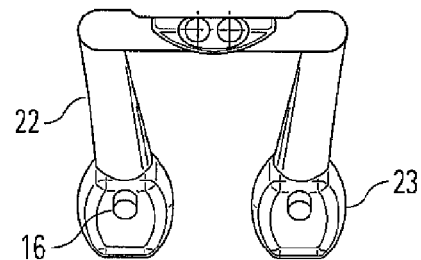
FIGS. 9-12 show views of the light guide holder with the transparent coupling body.
Figure 10:
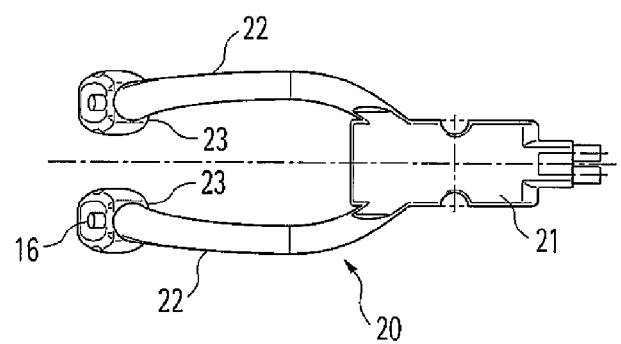
Figure 11:
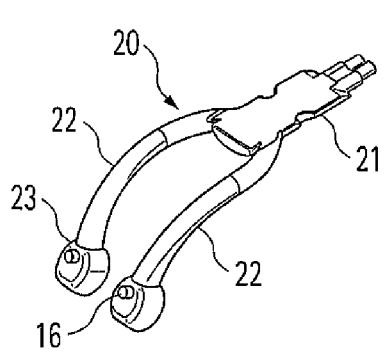
Figure 12:
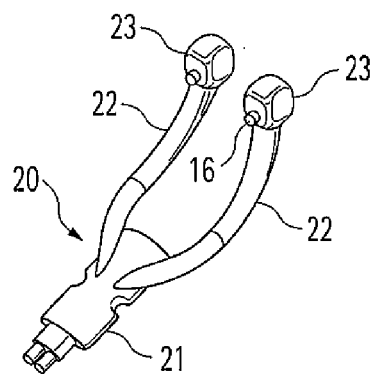
Figure 13:
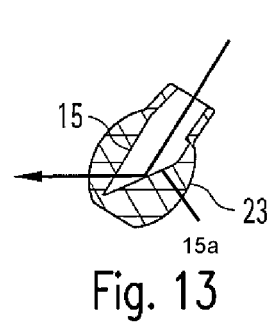
FIG. 13 shows the transparent coupling body with the deflecting prism located therein.
Figure 14:
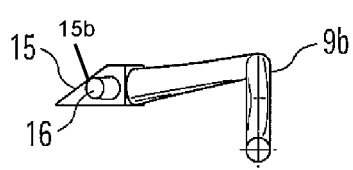
FIGS. 14 and 15 show views of the light guide with the deflecting prism located on it at the front end.
Figure 15:
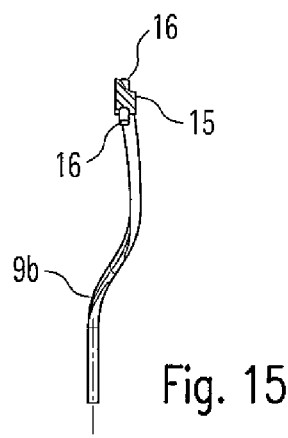

Firstly, FIGS. 5 to 8 show different views of the front end region of the attachment 10, the view of the outer sheathing of the attachment 10 having been omitted in FIGS. 6 and 7 so that the passage of the light guides can be seen. FIGS. 14 and 15 in turn show individual light guides 9b, which consist, for example, of plastics material, glass fiber bundles optionally with partially cemented fibers, single glass fibers, a fiber rod or similar materials and accordingly have a certain flexibility. The light guides 9b are connected at their fronts end with a deflecting prism 15 via which—as will be explained in greater detail hereinbelow—the light is deflected approximately perpendicularly and accordingly directed at the tooth to be examined. Coupling of the light guide 9b to the deflecting prism 15 can be carried out by injection-molding or the like.

An optical material whose refractive index is lower than the refractive index of the plastics light guide is preferably injection-molded around the flexible light guides 9b. As a result of this material, which can be, for example, self-adhesive silicone, the total reflection required for optimum light transmission is made possible.

For beam deflection, the deflecting prism 15 already mentioned is injection-molded at the exit end of the light guide 9b, it being possible for the deflecting prism 15 additionally to be provided with a coating on the reflection face 15a for the purpose of better transmission. The light exit side 15b could, in turn, additionally be provided with an optical lens structure, whereby it is possible to influence the light beam.

A particular feature is that the two—optionally sheathed—light guides 9b with the prisms 15 located thereon are embedded in a corresponding element which is referred to hereinbelow as the light guide holder 20 and is shown in greater detail in FIGS. 9 to 12. The light guide holder 20 firstly has a base portion 21 from the end region of which the ends of the light guides 9b extend. The light guides 9b initially run in parallel in the base portion 21, but they then branch into two arms 22 of the light guide holder 20, which extend towards the front end. At the front end, the arms 22 have head regions 23 in each of which the deflecting prisms 15 are arranged. To that end, two laterally projecting pins 16 are provided on the deflecting prisms, via which the prisms 15 are anchored in the end regions 23 of the light guide holder 20. At least the front end regions 23 of the light guide holder 20 are made of a transparent or light-permeable material, although the production of the light guide holder 20 as a whole is simplified if the entire element is made of the same transparent and flexible material.

The result of the embedding of the light guides 9b in the light guide holder 20 is that the light guides 9b are better protected from external influences. This is important because the light guide holder 20 is arranged on the attachment 10, which for hygiene reasons must be regularly cleaned, in particular also sterilized. Because the light guides 9b and the deflecting prism 15 are completely surrounded by the light guide holder 20, those optical elements for light transmission are better protected from external influences. An additional improvement in the protection can be achieved by preventing, or at least greatly reducing, the ingress of water into the light guide 9b by means of a suitable hydrophobic coating. The background to this improvement is that the light guide 9b, which is preferably sheathed in silicone, is exposed to a vapor overpressure atmosphere during autoclaving. By means of diffusion processes, the water passes through the outer layers of material into the plastics light guide 9b, which can lead to premature ageing or to damage in the form of the release of frozen-in stresses. By applying a hydrophobic layer, for which the material Parylene, for example, can be used, moisture is prevented from penetrating into the underlying components and damaging them. The hydrophobic layer can be applied either directly to the plastics light guide or to the outermost silicone layer of the plastics light guide sheathed in silicone.

Figure 16:
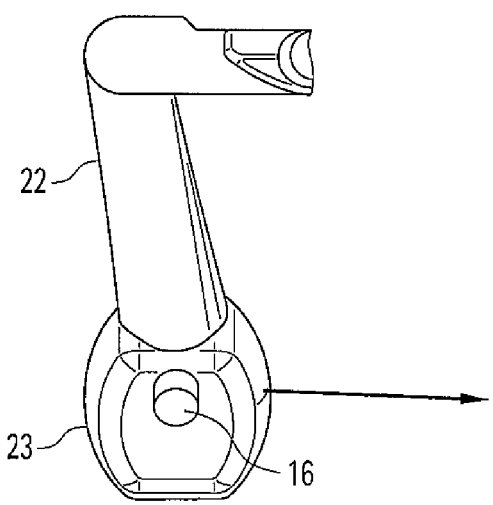
FIG. 16 shows schematically the delivery of the light via the coupling body.

A further advantage of the embedding of the light guides 9b and of the deflecting prisms 15 in the light guide holder 20 is that the coupling of light into the tooth to be examined can be optimized. As is shown by FIG. 16 and in particular also FIG. 13, which shows a sectional view of the front end region 23 of the light guide holder 20 with the deflecting prism 15 embedded therein, the light is ultimately irradiated into the tooth via the transparent end region 23, which is also referred to hereinbelow as the coupling body.

Because the coupling body 23 is made of a flexible transparent material, it can rest as flat as possible on the outside of the tooth or gingiva. This contact has the result that the formation of reflections or stray radiation, which could enter the entry window of the attachment 10 directly, is suppressed. Interfering reflections in the image of the illuminated tooth can thus be reduced. Flat application of the light coupling body 23 is preferably assisted by the fact that the arms 11 of the attachment 10 are also made of a flexible material and have a certain bias, as a result of which the arms 11 mould to the lateral walls of the tooth when in the fitted position thereon.

Figure 17:
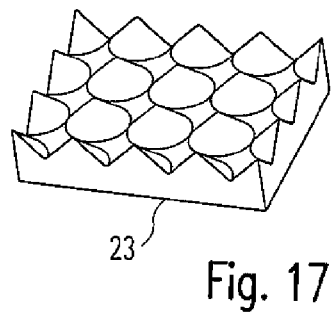
FIGS. 17 to 19 show different views of a structure located on the surface of the coupling body.
Figure 20:
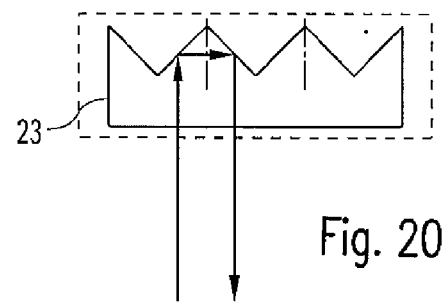
FIG. 20 shows the mode of operation of the structure provided on the coupling body.
Figure 18:
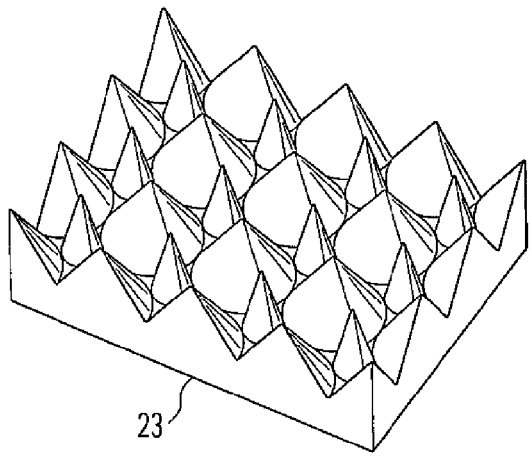
Figure 19:
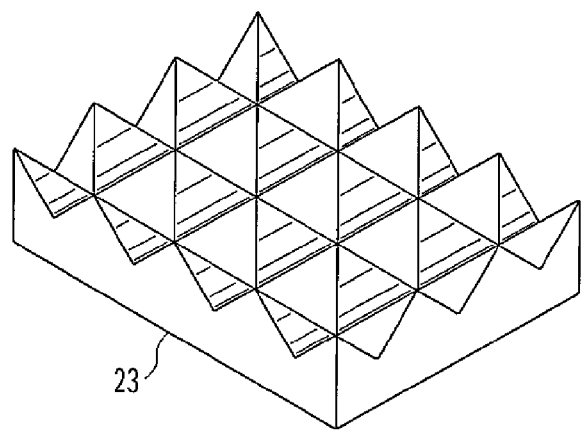
Figure 21:
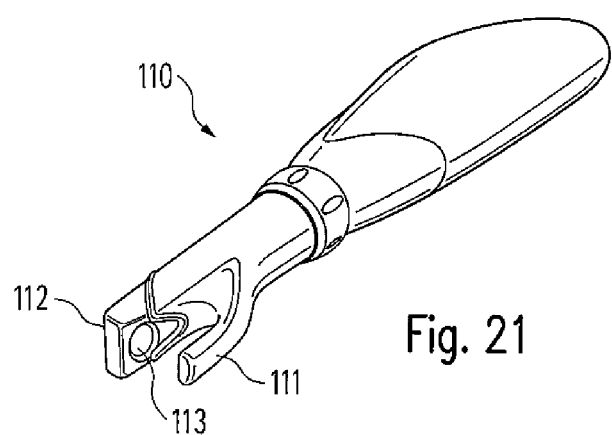
FIG. 21 shows a perspective view of an alternative attachment for light coupling and image acquisition of the device according to the invention.
Figure 22:
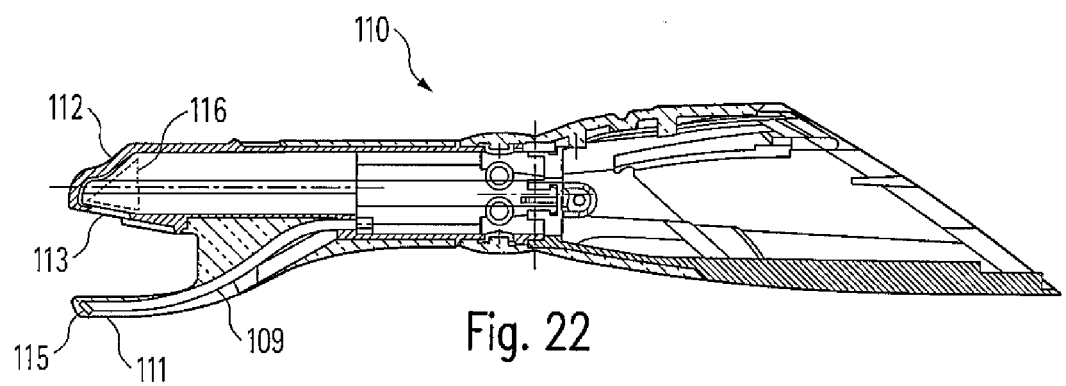
FIG. 22 shows a sectional view of the attachment of FIG. 20.
Figure 23:
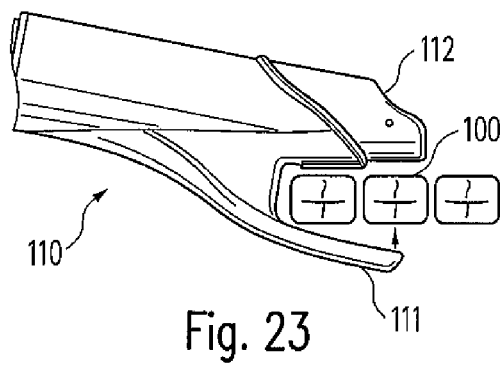
FIGS. 23 to 25 show systematic views relating to the use of the attachment of FIG. 21.
Figure 24:
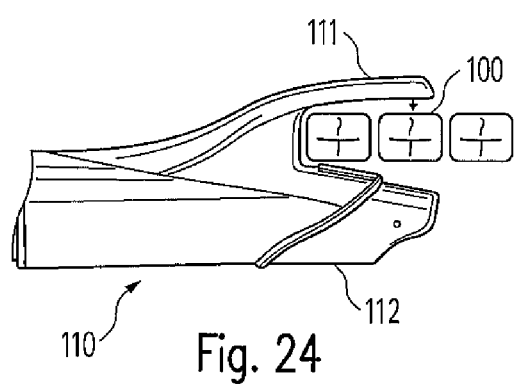
Figure 25:
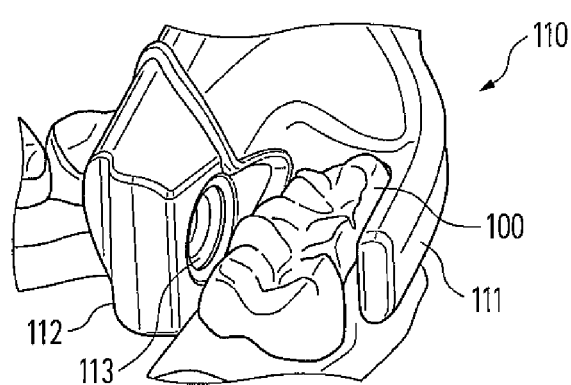

The coupling of light into the tooth can further additionally be optimized by a special form of the surface of the coupling body 23, which is initially approximately spherical. Conceivable surface structures therefore are shown in FIGS. 17 to 19. Geometries in the form of pyramids, cones, waves and waves with a corresponding structure which is distributed periodically and/or non-periodically can be used. The purpose of this structure is to improve further the coupling of the light into the hard tooth tissue and/or the gingiva and at the same time prevent light that cannot be coupled from being reflected at the hard tooth tissue and/or gingiva, which would lead to undesirable overexposure of the image-recording sensor. The mode of operation of this structure is based on the fact that light beams are partially deflected at the faces of the structures as long as the structures do not come into contact with the hard tooth tissue and/or the gingiva. This effect is based on the difference in refractive index between the contact material and air. This difference gives a corresponding angle of total reflection, light beams that are incident on the surface of the structure at a smaller angle being reflected back, as is shown schematically in FIG. 20. However, if the structure comes into contact with the hard tooth tissue and/or the gingiva, the geometrically determined light exit faces are deformed, which leads to a change in the angle at which the light beam is incident on the boundary surface. This in turn allows the light beams to leave the light coupling body 23 and pass into the hard tooth tissue.

A further possibility for avoiding overexposure would consist in the use of polarizing filters on both the light-exit side and the light-entry side and/or in the optical system of the detection device. The filters are so oriented that direct irradiation of the light-exit end on the light-entry side is prevented.

Finally, an advantage of the embedding of the light guides 9b with the deflecting prisms 15 in the light guide holder 20 is also that the light guide holder 20 can be replaced in a simple manner should this be necessary as a result of ageing phenomena. It is not necessary in this case to replace the entire attachment 10, for which reason the outlay in terms of cost for corresponding maintenance work can be reduced.

The measures described hereinbefore contribute in particular to achieving improved coupling of light into the tooth to be examined. A further improvement in the system can further also consist in using light having a comparatively small spectral bandwidth in the range from 2 to 10 nm. This has the advantage in particular that so-called speckle, which is caused by interference phenomena in human tissue, can be avoided or at least markedly reduced. This also contributes towards optimizing the results of the examination.

Finally, FIGS. 21 to 25 show a further attachment 110 which could be used in the device according to the invention for caries diagnosis. In contrast to the attachment 10 discussed hereinbefore, this further attachment 110 has only a single arm 111, through which there extends a light guide 109 having a deflection element 115 at the front end. The end region 112 having a light-entry window 113 is in turn arranged opposite the front end of the arm 111. When the attachment 110 is fitted to the handle 3 of the handpiece 2, the deflecting prism 116 is located directly behind the entry window 113, with the aid of which deflecting prism the light incident on the tooth 100 to be examined is directed to the image acquisition means.

The mutually opposing arrangement of the deflection element 115 and the light-entry window 113 has the result that, with the aid of the attachment 110, the tooth 100 to be examined can either be illuminated from the so-called buccal tooth surface and observed from the lingual tooth surface or alternatively illuminated from the lingual tooth surface and observed from the buccal tooth surface. Compared to embodiments conventional hitherto, such a changeover does not require the attachment to be replaced, which makes the operation much easier and represents a considerable time saving. Furthermore, it is also not necessary to remove the handpiece from the workspace, that is to say the oral cavity of the patient, and two-handed operation is not required in order to change the viewing direction. The attachment 110 is so arranged on the handpiece 2 that it cannot be twisted. Ergonomic handling is thereby achieved.

In this embodiment of the attachment 110 too, the light guide 109 having the deflection element 115 can be embedded in a transparent flexible element. That is to say, the above-described measures for improving the coupling of light into the tooth can also be used here.

Overall, therefore, a dental system for the transillumination of teeth is produced which allows images of very high quality to be produced, which ultimately leads to a marked improvement in the detection of caries.

The invention claimed is:
1. A dental system for the trans-illumination of teeth, comprising:
   a light source for producing examination radiation;

irradiation means for directing the examination radiation at a tooth to be examined;

means for acquiring an optical image of the tooth illuminated by the examination radiation; and a transparent, flexible coupling body configured to rest on the tooth or on a gingiva of the tooth, wherein the irradiation means includes one or more light-guiding elements and one or more light-deflecting elements, wherein at least one of the light-guiding elements is embedded in the material of the transparent, flexible coupling body, wherein the one or more light-deflecting elements comprise one or more deflecting prisms disposed proximate to an end of the one or more light-guiding elements, respectively, on a light-exit side, and wherein the flexible coupling body includes a light-transmitting structure adapted to deform when pressed against the tooth.

2. The dental system according to claim 1, wherein the coupling body comprises a plane face, a sphere, a spherical segment, a convex face, or a concave face, the light-transmitting structure arranged on the plane face, the sphere, the spherical segment, the convex face, or the concave face.

3. The dental system according to claim 1, wherein the coupling body is part of a light guide holder.

4. The dental system according to claim 3, wherein the light guide holder comprises a base portion and an arm extending outwardly from the base portion, the coupling body extending outwardly from the arm.

5. The dental system according to claim 1, wherein the one or more deflecting prisms are embedded in the coupling body.

6. The dental system according to claim 1, wherein a refractive index of the flexible coupling body is different than a refractive index of the light-guiding elements and/or the light-deflecting elements.

7. The dental system according to claim 1, wherein one or more of the light guiding elements have a hydrophobic coating.

8. The dental system according to claim 1, wherein the light source is configured to emit light having a spectral bandwidth in the range from 2 nm to 10 nm.

9. The dental system according to claim 1, further comprising a handpiece, the handpiece including a handle and an attachment removably coupled to the handle, wherein at least part of the irradiation means is arranged in the removable attachment, and wherein the attachment cannot be twisted relative to a longitudinal axis of the handpiece.

10. The dental system according to claim 1, comprising a handpiece and at least part of the irradiation means is arranged in a removable attachment, wherein the attachment cannot be twisted relative to the longitudinal axis of the handpiece.

11. The dental system according to claim 1, wherein one or more of the light-guiding elements have a sheathing having a hydrophobic coating.

12. A dental device for the trans-illumination of teeth, the dental device comprising:

a light source for producing examination radiation;

irradiation means for directing the examination radiation at a tooth to be examined; and a holding element for the irradiation means, the irradiation means being embedded within the holding element, the holding element having a base portion, one or more arms extending outwardly and downwardly from the base portion, and one or more flexible coupling bodies extending downwardly from the one or more arms, respectively, each of the one or more flexible coupling bodies configured to rest on the tooth or on a gingiva of the tooth, each of the one or more flexible coupling bodies including a light-transmitting structure adapted to deform when pressed against the tooth, wherein the irradiation means comprises one or more light guides and one or more deflecting prisms anchored disposed proximate to an end of the one or more light guides, respectively.

13. The dental device according to claim 12, further comprising a handpiece, the handpiece including a handle and an attachment removably coupled to the handle, wherein at least part of the irradiation means is arranged in the attachment.

14. The dental device according to claim 13, wherein the light source is arranged within the handpiece and the holding element is arranged on the attachment.

15. The dental device according to claim 12, wherein the one or more arms comprise a pair of arms, and wherein the one or more flexible coupling bodies comprise a pair of flexible coupling bodies extending downwardly from the pair of arms, respectively.

16. The dental device according to claim 12, wherein the one or more light guides are arranged within the base portion and the one or more arms, respectively, and the one or more deflecting prisms are arranged within the one or more flexible coupling bodies, respectively.

17. The dental device according to claim 16, wherein the one or more light guides comprise a first light guide and a second light guide, and wherein the one or more deflecting prisms comprise first and second deflecting prisms disposed proximate to an end of the first and second light guides, respectively, the first light guide routed through the base of the holding element and a first of the pair of arms, and the first deflecting prism arranged in a first of the pair of flexible coupling bodies, the second light guide routed through the base of the holding element and a second of the pair of arms, and the second deflecting prism arranged in a second of the pair of flexible coupling bodies.

* * * * *